(12) United States Patent
Price et al.

(10) Patent No.: US 9,414,872 B2
(45) Date of Patent: Aug. 16, 2016

(54) CONTOURED CALCANEAL PLATE AND A PERCUTANEOUS DRILL GUIDE FOR USE THEREWITH

(71) Applicant: ORTHOHELIX SURGICAL DESIGNS, INC., Medina, OH (US)

(72) Inventors: James P. Price, Stow, OH (US); Michael A. Zwolinski, Parma Heights, OH (US); Andrew J. Leither, Akron, OH (US); David B. Kay, Akron, OH (US); Bryan D. Den Hartog, Rapid City, SD (US); David B. Thordarson, Los Angeles, CA (US); John L. Marsh, North Liberty, OH (US); Derek S. Lewis, Copley, OH (US)

(73) Assignee: Orthohelix Surgical Designs, Inc., Medina, OH (US)

( * ) Notice: Subject to any disclaimer, the term of this patent is extended or adjusted under 35 U.S.C. 154(b) by 0 days.

(21) Appl. No.: 14/931,229

(22) Filed: Nov. 3, 2015

(65) Prior Publication Data

US 2016/0051299 A1 Feb. 25, 2016

Related U.S. Application Data

(62) Division of application No. 14/016,544, filed on Sep. 3, 2013, now Pat. No. 9,204,912.

(60) Provisional application No. 61/697,580, filed on Sep. 6, 2012.

(51) Int. Cl.
A61B 17/80 (2006.01)
A61B 17/88 (2006.01)
A61B 17/17 (2006.01)

(52) U.S. Cl.
CPC .......... *A61B 17/8061* (2013.01); *A61B 17/1728* (2013.01); *A61B 17/8057* (2013.01); *A61B 17/8085* (2013.01)

(58) Field of Classification Search
None
See application file for complete search history.

(56) References Cited

U.S. PATENT DOCUMENTS

| 4,903,691 | A | 2/1990 | Heinl |
|---|---|---|---|
| 5,690,631 | A | 11/1997 | Duncan et al. |
| 6,123,709 | A | 9/2000 | Jones |
| 6,235,032 | B1 | 5/2001 | Link |
| 6,348,052 | B1 | 2/2002 | Sammarco |
| D469,875 | S | 2/2003 | Bryant et al. |

(Continued)

FOREIGN PATENT DOCUMENTS

| DE | 3061715 | 7/1987 |
|---|---|---|
| WO | 2007127994 | 11/2007 |

*Primary Examiner* — Sameh Boles
(74) *Attorney, Agent, or Firm* — Duane Morris LLP

(57) ABSTRACT

This invention provides a calcaneal plate implanted using a sinus tarsi approach and comprises an anterior section having two locking screw holes, an s-shaped posterior facet section having a four locking holes and which rounds toward the bone at both the inferior and superior edges and is reinforced at the superior edge, and a blade shaped posterior portion having three linearly aligned locking holes and terminating in a tapered portion. There is also, a drill guide assembly having a drill guide column inserted through a hole in a targeting guide and locking to one of the locking holes in the plate, and cannulated drill guide sleeves that lock into holes in the targeting guide in a spaced relation whereby when the targeting guide is locked into the plate, the targeting guide can be used as a handle and wherein locking screws can be implanted percutaneously.

4 Claims, 8 Drawing Sheets

(56) References Cited

U.S. PATENT DOCUMENTS

| | | |
|---|---|---|
| D480,141 S | 9/2003 | Benirschke et al. |
| 7,229,445 B2 | 6/2007 | Hayeck et al. |
| D580,057 S | 11/2008 | Ramadani |
| D589,149 S | 3/2009 | Strnad et al. |
| 7,846,189 B2 | 12/2010 | Winquist et al. |
| 2006/0015102 A1 | 1/2006 | Toullec et al. |
| 2006/0173458 A1 | 8/2006 | Forstein et al. |
| 2006/0235396 A1 | 10/2006 | Sanders et al. |
| 2006/0241609 A1 | 10/2006 | Myerson et al. |
| 2007/0123869 A1 | 5/2007 | Chin et al. |
| 2007/0162020 A1 | 7/2007 | Gerlach et al. |
| 2008/0021452 A1 | 1/2008 | Ducharme et al. |
| 2010/0057133 A1 | 3/2010 | Simon |
| 2010/0217327 A1* | 8/2010 | Vancelette ......... A61B 17/8061 606/281 |

\* cited by examiner

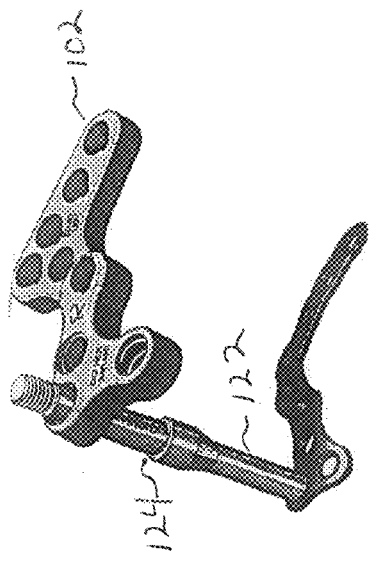
FIG. 7
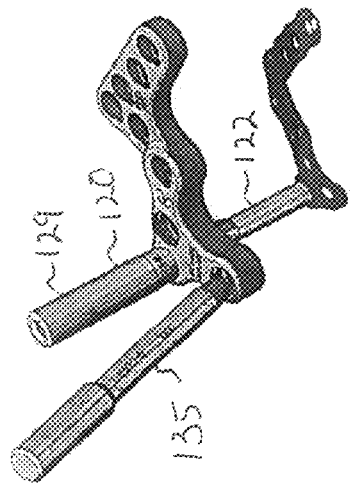
FIG. 9
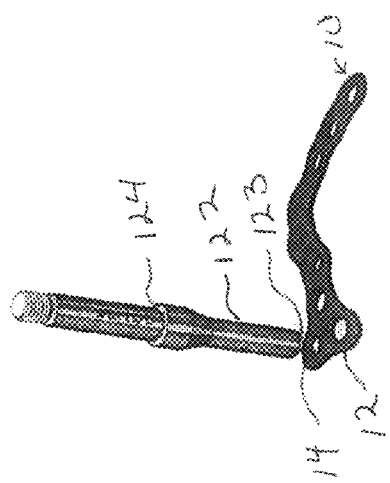
FIG. 6
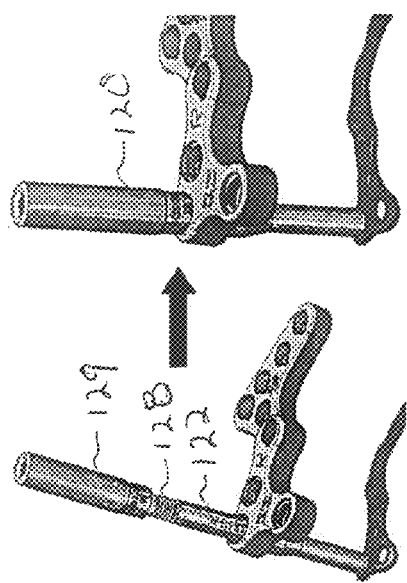
FIG. 8a
FIG. 8b

CONTOURED CALCANEAL PLATE AND A PERCUTANEOUS DRILL GUIDE FOR USE THEREWITH

CROSS REFERENCE

This application is a divisional application of U.S. application Ser. No. 14/016,544, filed on Sep. 3, 2013, which claims the benefit of priority under 35 U.S.C. §119 of U.S. Provisional Application Ser. No. 61/697,580, filed on Sep. 6, 2012, herein fully incorporated by reference.

THE FIELD OF THE INVENTION

The present invention relates to a less invasive fully contoured orthopedic implant for use in fixation of a calcaneus, to a drill guide assembly which can be used as an aid in implanting the implant and for percutaneous implantation of the screws used with the plate, and for a novel method of implanting an orthopedic plate. The present invention is designed for use for stabilization and/or reconstruction following the most common fracture to the hindfoot joint, i.e., calcaneal fractures of which the most common is a Sander's type II fracture. This type of fracture generally comprises an interior to lateral fracture, which often results in a three-part fragmentation of the calcaneus often leaving the sustentaculum as the healthiest fragment and displacing laterally and posterior the remaining fragments of the calcaneus. In addition, the plate of the present invention can be used for osteotomies and fixation of other fractures or reconstruction due to trauma or deformities.

BACKGROUND OF THE INVENTION

Implants have been provided in the past to try to help stabilize the fragments in order to allow the calcaneus to fuse, and more recently these attempts have provided fairly robust plates that can be used for reduction of the bone fragments and further which allow for relatively quick use of the injured limb through the support of the implant. For some situations, these plates remain ideal; however, these prior art plates require a large and relatively invasive surgery and displacement of sensitive soft tissue to access the bone. The implant of the present invention is designed for implantation in appropriate cases through a small incision inferior to the lateral malleolus where the posterior end of the implant can be slipped into position using a drill targeting guide that is spaced an appropriate distance in an offset parallel position (i.e., from about 0.5 to about 3 inches) from and parallel to the implant so that it can be used like a handle to slip the plate into position adjacent the calcaneus. The relationship between the drill targeting guide and the implant is created and maintained by one of more individual drill guide column assembly, which interlock into one or more selected screw holes of the implant and form a spaced relationship between the implant and a drill targeting guide. Cannulated drill guide sleeves lock in a position in the drill targeting guide and engage other screw holes in the implant (e.g. through minimal incisions or through the skin) to allow for pilot holes to be drilled for ultimate placement of a fastening screw.

Thus, the present invention provides several aspects, which include a novel implant (or plate design), a drill guide assembly, and a method of enabling or performing a hindfoot surgery.

The implant comprises a fully contoured plate which has a ribbon shape (as used herein to mean that the plate is elongate although curving along a length of screw holes, and has a generally uniform width that accommodates the diameter of the screw holes, and further is advantageously diminished somewhat between the holes) with a taper at one end. The plate further has an undulating profile which can be envisioned as an anterior tab having a superior and anterior locking hole and relative to the first hole, an inferior and posterior locking hole which provide for multiplanar fixation. Next, there is a gently s-shaped section having a plurality of locking holes (preferably four) where the profile of the plate section accommodates and supports the posterior facet, The third section of the plate can be based on a series of aligned locking holes that form a linear posterior tab having two to five, and preferably three spaced holes. This blade shaped section of the plate is the posterior section that can be slipped into position adjacent the calcaneus through a small incision inferior to the lateral malleolus. The plate has a bottom surface that faces the bone which includes radiused sections corresponding to the profile sections described above. The anterior tab is curved inferior to superior in a shape which is close to cylindrical and which approximates the shape of the anterior process of the calcaneus. The second section is curved about a different axis so that the plate appears to wrap in the superior direction where it supports the posterior facet. The third portion, i.e. the posterior blade curves about an axis that intersects the screw holes so as to form a portion of a cylinder.

The intermediate portion of the plate includes four locking holes which are internally threaded and are designed to directly support the subtalar joint fragment, specifically just inferior to the posterior facet (i.e. the articulating surface) of the calcaneus. Optionally, the plate further includes smaller holes which allow the use of K wires both for reduction of the fragments, and for further fixation.

In addition, while both the bone facing surface and the outwardly facing surface of the plate are smooth and uninterrupted (other than by the fixation holes) the intermediate portion has an area of increased thickness to provide a reinforced portion in the vicinity of the posterior facet. This area is where the majority of the weight transfer from the tibia to the talus to calcaneus occurs. The plate is provided in a right and a left version and is generally used on the lateral portion of the calcaneal bone situated slightly posterior to the cuboid slightly inferior to the posterior facet, and supported on the posterior portion of the calcaneus. The plate is also provided in multiple profiles for small and large patients.

As a further aspect, the invention relates to a drill guide assembly that includes a flat (i.e. planar) targeting guide which mimics the profile or outline of the plate and is provided with through holes that accept drill columns to connect the targeting guide and the plate. These "drill columns" comprise drill column assemblies which have a top and a bottom that assemble through a hole in the targeting guide to lock the targeting guide intermediate the drill column assembly, drill assembly columns which are single units that lock into the implant and support the targeting guide in a defined relationship, drill sleeves that are held and preferably locked into the targeting guide and are cannulated for insertion of drills, screws or other appropriately sized drill guides. At least one of the drill columns have an end that can be secured in a locking hole of the plate, for example by providing threads that mate with the threaded locking hole of the plate. Further, the external surface of this drill column assembly includes means to secure the targeting guide at a fixed distance from the plate, for example, by providing the external surface of the drill column with a shoulder that forms a flange on which the bottom surface of the targeting guide will rest. An internally threaded sleeve can then be secured over the drill column and screwed onto external threads on the drill column to lock the targeting guide on the drill column so that it will not move. Preferably a second drill assembly column is used to secure this relationship which allows the targeting guide to be used like a handle so that a tapered end of the implant can be slipped into a minimal incision for positioning adjacent the relevant bone surface.

BRIEF DESCRIPTION OF THE DRAWINGS

The Invention Will be Better Understood and Other Features and Advantages Will Become Apparent by Reading the Detailed Description of the Invention, Taken Together with the Drawings, Wherein:

FIG. 6 is a top end view of a first drill column assembly bottom component being assembled with the plate of FIG. 1;

FIG. 7 is a top end view of the plate and drill column of FIG. 9 and including the addition of the targeting guide on the drill guide bottom component;

FIGS. 8(a) and 8(b) are top end views showing the sequential assembly of the top and bottom components of the drill guide columns to lock the targeting guide between the top and bottom components of the drill guide column assembly;

FIG. 9 is a top side view showing the insertion of an integral drill assembly column through a further hole in the anterior portion of the targeting guide;

DETAILED DESCRIPTION OF THE INVENTION

Figure 4:
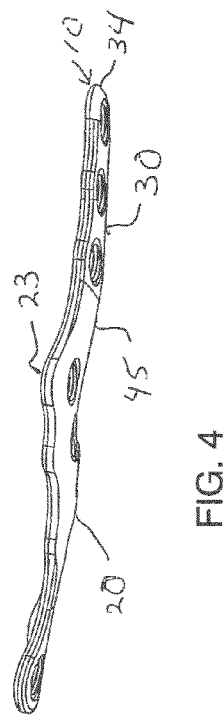
FIG. 4 is a side view of the plate of FIG. 1 taken from the superior side and with the bone facing side of the plate up.
Figure 1:
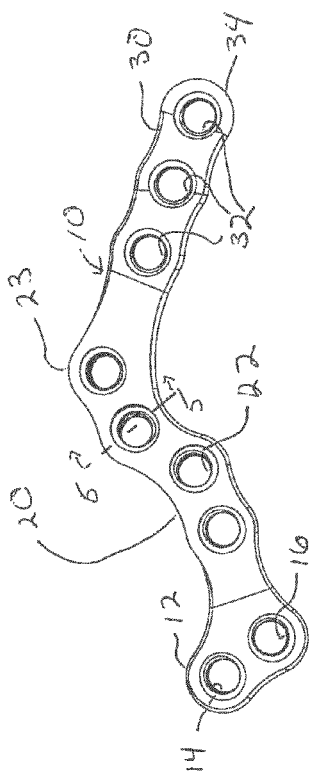
FIG. 1 is a top view of the plate in accordance with the invention.
Figure 2:
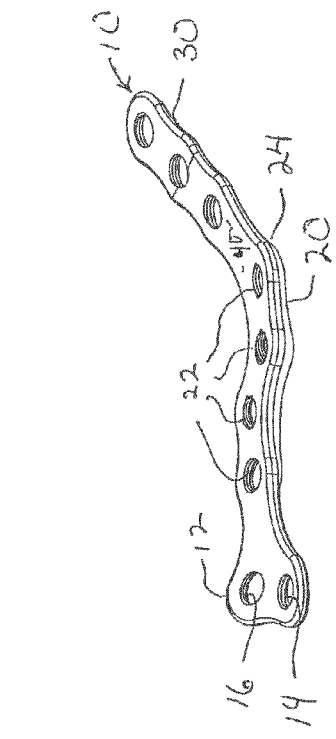
FIG. 2 is a bottom view of the plate of FIG. 1.
Figure 3:
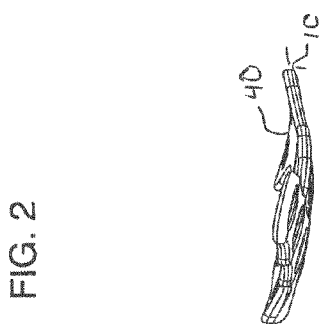
FIG. 3 is a top end view of the plate of FIG. 1 taken from the posterior end.

The implant of the present invention is a less invasive calcaneal plate shown from the top in FIG. 1 at 10. The plate 10 has an undulating profile which can be envisioned as an anterior tab 12 having an internally threaded superior and anterior locking hole 14 and relative to the first hole, an internally threaded inferior and posterior locking hole 16 which provide for multiplanar fixation. Attached to this is a posterior facet supporting section 20 which has a serpentine shape and a plurality of locking holes 22 (preferably four) where the profile of the plate section accommodates and supports the loading at the posterior facet, Further as may be viewed in FIG. 4, the superior most portion 23 of the posterior facet section 20 tapers in thickness and wraps inward in the direction of the bone facing surface so that the plate contouring in the Z direction accommodates a generalized shape of a calcaneus, and avoids edges that would provide places for soft tissue, and in particular for the tendons to hang up. Further the plate is reinforced by providing for additional thickness along the edge 24 and into the plate below the locking holes in the posterior facet section. The third section of the plate or posterior tab 30 can be based on a series of aligned locking holes 32 that form a linear posterior tab having two to six, and preferably three or four spaced locking holes. The end of this blade shaped section is rounded in profile and tapers to a narrow edge 34 which further enables the plate to be slipped into position adjacent the calcaneus through a small incision inferior to the lateral malleolus.

The plate 10 has a bottom surface 40 that faces the bone which includes radiused sections corresponding to the profile sections described above. The anterior tab 12 is curved inferior to superior in a shape which is close to cylindrical and which approximates the shape of the anterior process of the calcaneus bone. The posterior facet section 20 is curved about a different axis so that the plate appears to wrap in the superior direction where it supports the anterior facet. The third portion, i.e. the posterior blade section 30, curves about an axis that intersects the screw holes so as to form a portion of a cylinder.

Figure 5:
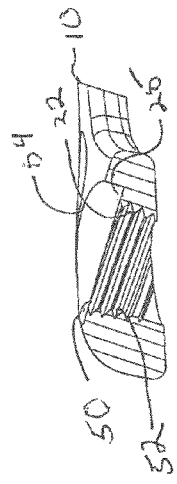
FIG. 5 is a detail of a screw hole taken in cross section along line 5-5 of FIG. 1.

The intermediate portion of the plate includes locking holes which are designed to directly support the subtalar joint fragment, specifically just inferior to the posterior facet (i.e. the articulating surface) of the calcaneus. As is illustrated in FIG. 5, these holes are angled through the plate, and include a counterbore section 25 that forms a seat for the drill guide sleeve. Optionally, the plate can further include smaller holes which allow the use of K wires both for reduction of the fragments, and for further fixation.

Figure 20:
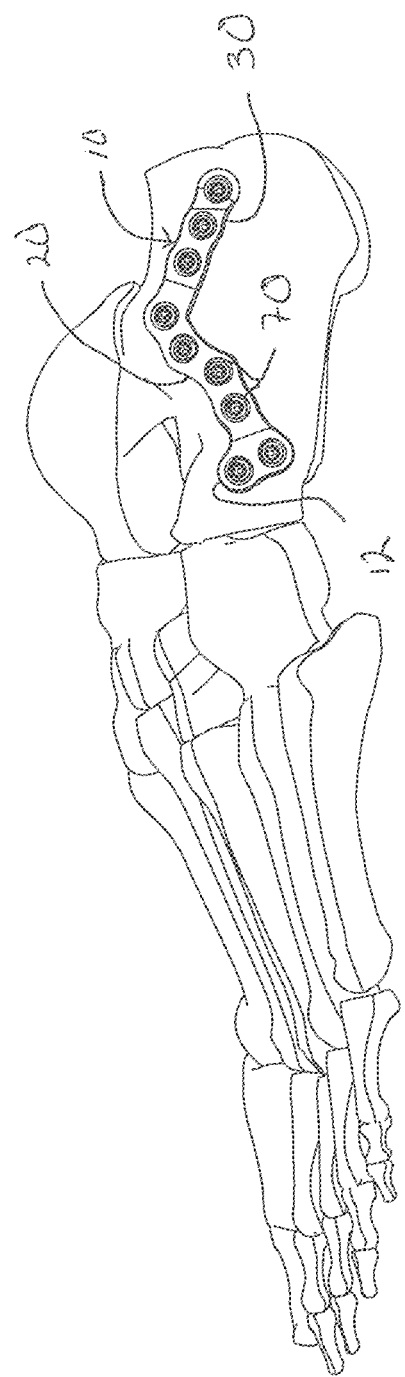
FIG. 20 is a top view of the implant of the present invention in position on a calcaneus.
Figure 21:
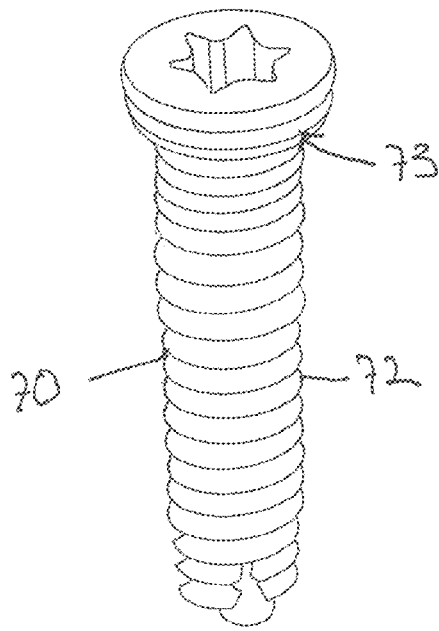
FIG. 21 is a side view of a locking screw to be used with the plate of the present invention.
Figure 22:
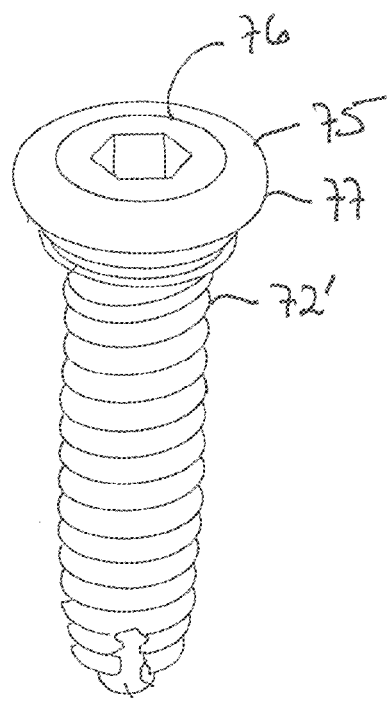
FIG. 22 is a side view of a variable locking screw assembly to be used with the plate of the present invention.

In addition, while both the bone facing surface 40 and the outwardly facing surface 45 of the plate are smooth and uninterrupted (other than by the fixation holes) the intermediate portion has an area of increased thickness 24 to provide a reinforced portion in the vicinity of the posterior facet. This area is where the majority of the weight transfer from the tibia to the talus to calcaneus occurs. The plate is provided in a right and a left version and is generally used on the lateral portion of the calcaneal bone situated slightly posterior to the cuboid slightly inferior to the posterior facet, and supported on the posterior portion of the calcaneus as is shown in FIG. 20. The plate is also provided in multiple profiles for small and large patients. The plate is made of an appropriate biocompatible material, such as titanium, or surgical grade stainless, or a biocompatible non-metallic material such as ceramic or PEEK.

A detail of the locking screw holes is shown in FIG. 5. This illustrates the screw hole here numbered 50 which is representative of each of the locking screw holes of the plate 10, and shows the internal threads 52, along with a recessed counterbore 54 which provides a surface for the seating of the end of a drill column so as to define a fixed locking angle intended to provide for locking at an angle that is meant for optimal reduction in a typically fractured generalized calcaneus.

The screws used in the construct in accordance with the present invention are shown in FIGS. 17-19 and 21 and 22. These screws 70 can include a fixed angle locking screw having a cancellous thread 72 and a threaded locking head 73 which includes threads that lock with the internal threads of the screw holes of the plate. Alternatively, the screws can comprise a variable angle locking assembly 75 that has a screw with a cancellous section 72' and a threaded head 76 that mates with a locking insert 77 which is threaded into the screw hole of the plate to allow locking of the screw in the plate at a selected variable angle or a non-locking screw can be used, such as a screw having a rounded head 4 that rides on the internal threads of the screw hole of the plate to compress the plate toward the bone with the screw in a non-locked relationship to the plate. The screws are provided in a variety of lengths in order to best accommodate the area of attachment of the plate.

As a further aspect, the invention relates to a drill guide assembly 100 that includes a flat (i.e. planar) targeting guide 102, which mimics the profile or outline of the plate and is provided with through holes 104 that accept one or more drill columns 120 to connect the targeting guide 102 and the plate 10 at a spaced fixed relationship. The initial fixed drill column assembly 121 can be constructed of a bottom component 122 which includes a first end having means, and specifically locking threads 123 to lock the bottom drill component into a screw hole (in this case the superior hole 14 of the anterior section 12) in the plate 10. The bottom drill guide component 122 also has a shoulder 124 defining an annular flange that forms a seat for the targeting guide 102. The bottom drill guide component includes an upper portion with threads 128 that are engaged by internal threads in the top of a top component 129 of a drill column assembly The inner diameter of the top component (below the threads) is oversized for clearance. The bottom end of the upper portion 129 is sized to engage a cylindrical seat concentric with the hole on the implant opposing side of the targeting guide.

Figure 11:
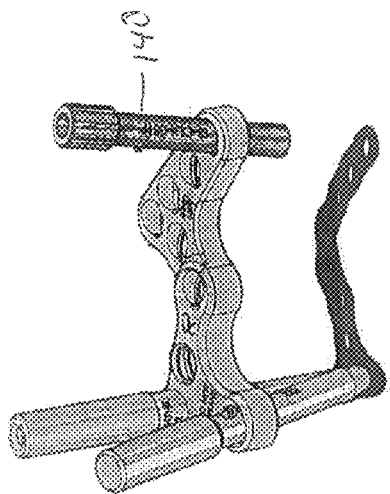
FIG. 11 is a top side view showing the addition of a drill sleeve which enables the positioning is a pilot hole or screw using the drill guide assembly in accordance with the present invention.
Figure 10:
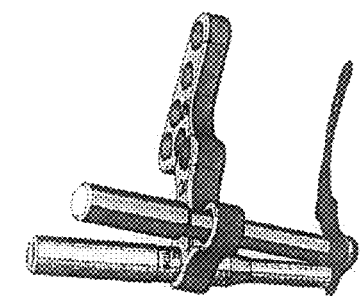
FIG. 10 is a top end view showing the spaced relationship of the plate and the targeting guide assembled using a drill column assembly and an integral drill assembly column.
Figure 12:
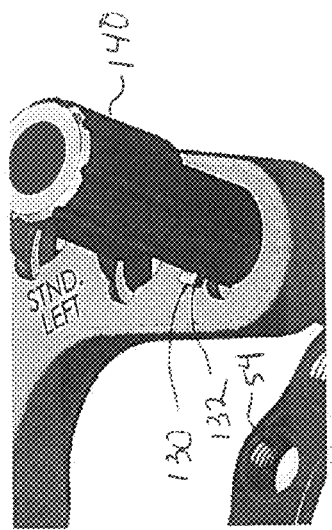
FIG. 12 is a close up view showing the detail of a locking mechanism, which locks the drill column to the targeting guide.
Figure 14:
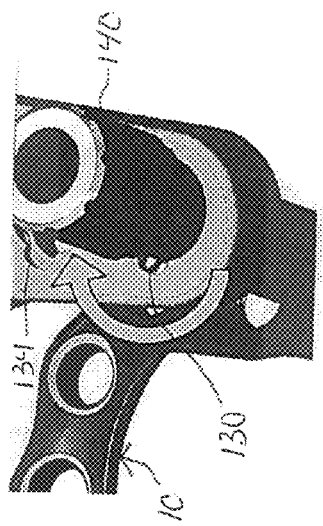
FIG. 14 is a top view of the drill sleeve illustrating the locking head.
Figure 15:
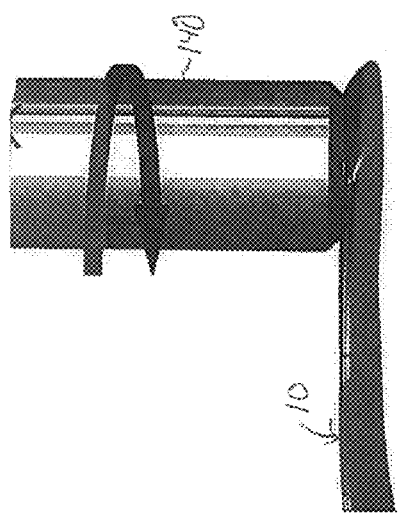
FIG. 15 is a side view of the drill sleeve illustrating locking of the externally threaded end of the drill sleeve in the internal threads of the plate.
Figure 13:
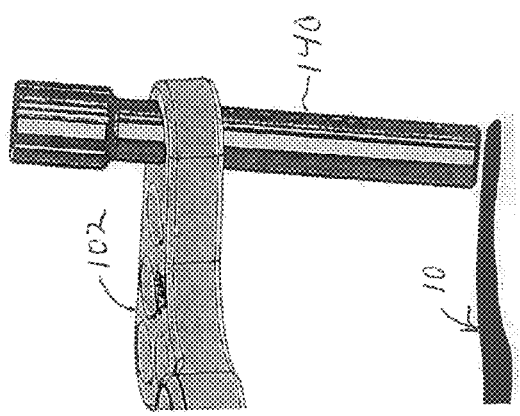
FIG. 13 is a side view of the drill guide assembly showing the drill sleeve being lowered into position relative to the plate.
Figure 16:
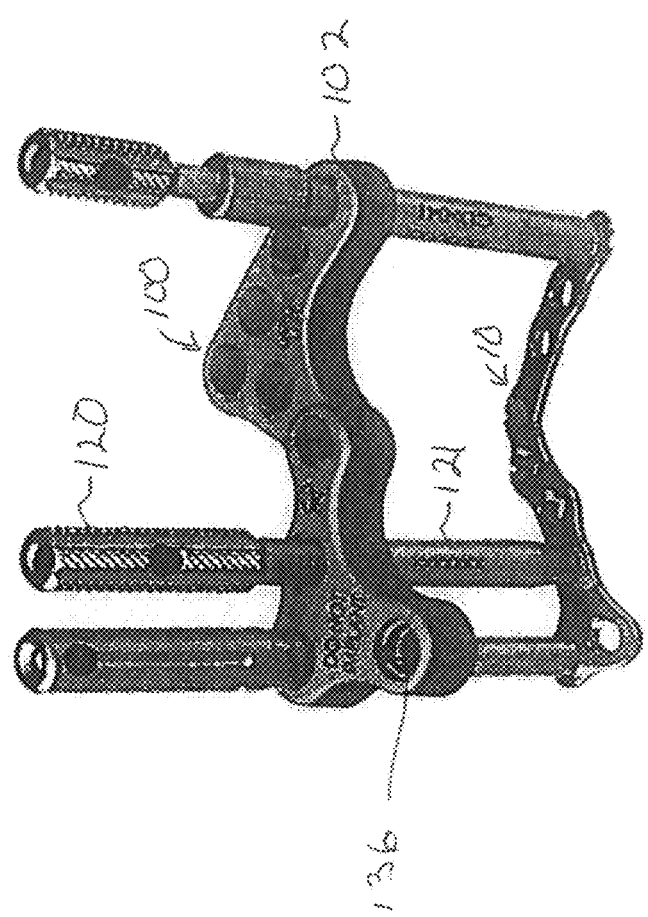
FIG. 16 is a view of the drill guide assembly from FIGS. 6-15 further including a drill guide positioned in the posterior most hole of the plate.
Figure 19:
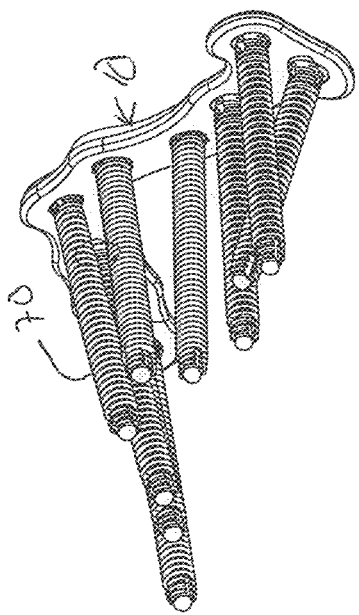
FIG. 19 is a bottom end view of the plate and screws shown in FIG. 17.
Figure 17:
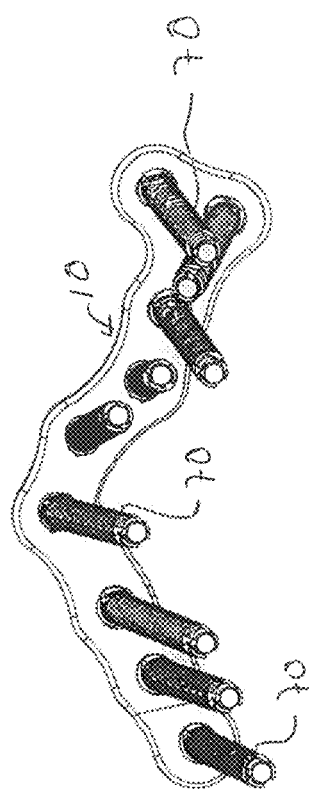
FIG. 17 is a bottom view of the implant of the present invention including a full set of fixed angle locking screws.
Figure 18:
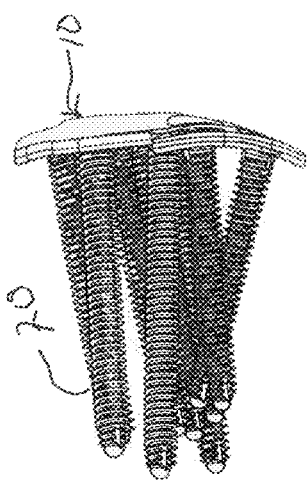
FIG. 18 is an end view of the plate and screws shown in FIG. 17.

A second drill guide assembly column 135 can be inserted through a second hole in the targeting guide as is shown in FIG. 9 and locked into a fixed relation using the locking means previously discussed which provides the construct shown in FIG. 10. This allows the targeting guide to be used, like a handle, to insert the tapered end of the plate into a minimal incision to place the plate adjacent the bone. FIGS. 11 and 12 show the additional assembly by sliding through a specifically angled hole of one or more cannulated drill sleeves 140 in the targeting plate (the drill sleeve 140 includes locking means 130, comprising a boss member 132 which engages an undercut 136 in the targeting guide hole as shown in FIG. 15 to lock the drill sleeve 140 in position relative to the targeting guide 102 so that a screw can be feed through the drill sleeve and into contact with the locking hole of the plate). This view further illustrates the counterbore 54 in the top surface of the plate and surrounding the threaded holes 50 to allow the tapered end of the drill sleeve to seat at the desired angle by forming the surface defined by the counterbore at that angle. It should be noted that the drill sleeve can be added to the plate when the plate is in position against the bone. The surgeon has the option of making a small incision that corresponds to the positioning of the screw before using the drill sleeve or after using a specially adapted scalpel. Further additional flesh can be removed using a trocar through the drill sleeve and the screw can be added percutaneously through the small incision into position in the plate.

When used in surgery, the patient is placed in a lateral decubitus position. Advantageously, the plate and assembly of the present invention permit the use of the Sinus Tarsi approach which allows for direct access to the subtalar joint and subsequently good anatomic reduction of the joint, but with less morbidity than with a larger lateral extensile approach. In this approach, a 3-4 inch incision is made, i.e. an incision of not more than 4 inches, and preferably only about 3 inches or is limited to 3 inches in length, that begins posteriorly, below the lateral malleolus and travels diagonally downward on the lateral side of the foot toward the calcaneocuboid joint. Thus, the incision is more or less centered between the sural nerve and the superficial peroneal nerve. The resulting incision can be opened to allow the posterior blade end of the plate to be inserted toward the posterior end of the calcaneus and under the sural nerve by slipping it into the incision and under the soft tissue. (This contrasts with prior art techniques in which a large incision was made to expose a wide section of bone, i.e. more than 5 inches long and being a width of more than 1 inch such as an I shape). The posterior facet section of the plate can be viewed through the incision, and the screws can be added to the anterior section as discussed above percutaneously. The plate of the present invention include right and left versions and further may include plates having a variety of sizes and shapes to accommodate variations in the population. The plate is placed at the appropriate position on the lateral calcaneal wall. The plate is contoured to accommodate most calcaneal surfaces; however, the plate can further be contoured by a surgeon if he or she deems it necessary. While in accordance with the patent statutes, the best mode and preferred embodiment have been set forth, the scope of the invention is not limited thereto, but rather by the scope of the attached claims.

While in accordance with the patent statutes the best mode and preferred embodiment have been set forth, the scope of the invention is not limited thereto, but rather by the scope of the attached claims.

What is claimed is:

1. A method of performing a calcaneal surgery on a calcaneus comprising the steps of forming a sinus tarsi incision on the lateral side of an ankle; selecting a calcaneal plate having an anterior section having a locking screw hole and a posterior section having a screw hole, locking a drill guide column in the locking screw hole of the anterior section; locking a targeting guide having a through hole about the drill guide column in a spaced relation; using the targeting guide as a handle to insert the posterior section of the calcaneal plate through the sinus tarsi incision; and locking a further drill guide which is cannulated to the targeting guide and implanting a screw through that drill guide to fix the calcaneal plate relative to the calcaneus; wherein the screw is implanted percutaneously; and wherein the plate has a generally uniform thickness and the posterior section has a thickness greater than the uniform thickness to accommodate weight transfer from tibia to talus to calcaneus.

2. A method of performing a calcaneal surgery as set forth in claim 1, wherein the sinus tarsi incision is not more than 4 inches in length.

3. A method of performing a calcaneal surgery as set forth in claim 1 wherein the posterior section has a tapered end.

4. A method of performing a calcaneal surgery as set forth in claim 1 wherein the targeting guide has a plurality of holes, and the calcaneal plate has a plurality of holes and the number of targeting guide holes corresponds to the number of calcaneal plate holes.

* * * * *